United States Patent [19]

MacKay et al.

[11] Patent Number: 5,760,312

[45] Date of Patent: Jun. 2, 1998

[54] DEVICE AND METHOD FOR DETERMINING INTERNAL PRESSURE IN A PRESSURIZED BALL

[76] Inventors: H. Bruce MacKay, 3323 Carleton St., San Diego, Calif. 92106; Daniel J. Bozich, P.O. Box 1997, Mammoth Lakes, Calif. 93546

[21] Appl. No.: 754,632

[22] Filed: Nov. 21, 1996

[51] Int. Cl.[6] .................................................. G01N 3/08
[52] U.S. Cl. .................................................. 73/818; 73/81
[58] Field of Search ............................... 73/81, 763, 781, 73/818

[56] References Cited

U.S. PATENT DOCUMENTS

| | | | |
|---|---|---|---|
| 4,114,350 | 9/1978 | Snyder | 53/79 |
| 4,136,554 | 1/1979 | Larson | 73/81 |
| 4,251,073 | 2/1981 | Birdsong et al. | 273/61 |
| 4,313,289 | 2/1982 | Birdsong, Jr. | 53/84 |
| 4,555,028 | 11/1985 | Valehrach | 209/599 |
| 4,590,808 | 5/1986 | Lighfoot et al. | 73/862.47 |
| 4,876,658 | 10/1989 | Hass | 364/550 |
| 5,222,391 | 6/1993 | Reenstra | 73/81 |
| 5,291,774 | 3/1994 | Putnam, Jr. | 73/82 |
| 5,372,030 | 12/1994 | Prussia et al. | 73/37 |
| 5,511,410 | 4/1996 | Sherts | 73/81 |
| 5,567,870 | 10/1996 | Harris | 73/81 |
| 5,639,969 | 6/1997 | D'Adamo | 73/818 |

*Primary Examiner*—Hezron E. Williams
*Assistant Examiner*—Jay L. Politzer
*Attorney, Agent, or Firm*—Brown, Martin, Haller & McClain

[57] ABSTRACT

A pressurized ball testing device for determining the relative pressure of tennis balls or other inflated balls whose internal pressure cannot be directly measured comprises a housing having two half shells, attached along a common axis so that the two half shells are movable along the central axis relative to each other. The interior of each half shell has a ball support centered on the central axis. The ball to be measured is placed between the two ball supports so that when the two half shells are pressed together, the ball is simultaneously compressed and held in place. The pressures are relative to a new ball or reference ball, allowing the balls to be sorted for suitability of play. Two methods of measurement are described, one using constant force and the other using constant displacement. In either case the ball to be tested is squeezed from opposite sides by finger-like protrusions to enhance the displacement of the side of the ball for a given force.

20 Claims, 5 Drawing Sheets

DEVICE AND METHOD FOR DETERMINING INTERNAL PRESSURE IN A PRESSURIZED BALL

BACKGROUND OF THE INVENTION

In the game of tennis, the pressure of the tennis ball is an important factor in determining how well the ball bounces off the court surface or the face of the tennis racquet. Accordingly, a player wants to practice or play with balls that have more than an arbitrary minimum pressure and are matched in pressure within a nominal range. Balls from a freshly opened can are generally guaranteed to be of uniform pressure with maximum bounce, but for frequent players, using a new can of balls for every match is expensive and wasteful. Instead, players often meet for a game with several previously opened cans of balls and must sort out the best ones for play. Similarly, a basket of used balls for practice play or use in a ball machine needs to be sorted regularly to remove the flat ones. In these situations, a quick, effective means of accurately measuring relative ball pressures for objective sorting is needed.

The problem is that tennis balls do not have pressure valves, and therefore a direct measurement of internal pressure is not possible as it is for a basketball or football. Most tennis players resort to a subjective bounce or squeeze test with less than satisfying results, especially when testing large quantities of balls. Accordingly, there is a need for a simple yet objective device and method for determining the relative pressure of a tennis ball quickly and easily. It is to such a device and method that the present invention is directed.

SUMMARY OF THE INVENTION

In an exemplary embodiment, the device for determining the relative pressure of tennis balls or other inflated balls whose internal pressure cannot be directly measured comprises a housing having two half shells, attached along a common axis so that the two half shells are movable along the central axis relative to each other. The interior of each half shell has a ball support centered on the central axis. The ball to be measured is placed between the two ball supports so that when the two half shells are pressed together, the ball is simultaneously compressed and held in place. The measured ball pressures are relative to a new ball or reference ball, allowing the balls to be sorted for suitability of play. Two distinct methods of measurement are described; one uses constant force and the other uses constant displacement. In either case the ball to be tested is squeezed from opposite sides by finger-like protrusions, instead of a flat surface, to enhance the displacement of the side of the ball for a given force. In the constant force method, the protrusions are pressed into the ball with a set force and their resulting displacement into the ball indicates the relative ball pressure. In the second method, the ball is squeezed by a fixed displacement, and the resulting force indicates the ball pressure.

An exemplary embodiment for each method is presented, both of which, in their preferred embodiments use concentric, sliding cylinders. Each cylinder is closed at the one end and contains a protrusion. These cylinders slide together forming a closed can to constrain the ball between the protrusions and allow the protrusions to be pressed into the ball from opposite sides. In both embodiments, one of the protrusions is mounted on a piston-like disk that can slide in the cylinder, but is pressed against a stop by a pre-compressed spring between the disk and the closed end of the cylinder.

In the constant force embodiment, the spring is pre-compressed to the desired set force. The other protrusion is manually pushed into the ball until the applied force matches the pre-compressed spring force, causing the inner spring/protrusion to move backward slightly and activate an alarm means. At this point, the relative displacement of the two cylinders, as shown by a scale on the outer cylinder indicates the ball pressure. The scale is calibrated using a new ball or reference ball by adjusting the spring pre-compression force.

In the constant displacement embodiment, the cylinders are pressed together until a stop is reached at a fixed displacement. The low end of the scale is calibrated by pre-compressing the spring to the force of a bad ball. Testing balls of higher pressure will compress the spring further, whereas testing balls of lower pressure will not compress the spring. The spring compression is measured by a linear transducer, which changes the mechanical motion into an electrical signal that is electronically displayed on an LED bar graph. The high end of the bar graph scale which indicates the most spring compression or ball pressure can be set electronically with a potentiometer adjustment by using a new ball for calibration.

BRIEF DESCRIPTION OF THE DRAWINGS

The present invention will be better understood from the following detailed description of a preferred embodiment, taken in conjunction with the accompanying drawings, in which like reference numerals refer to like parts, and in which.

DESCRIPTION OF THE PREFERRED EMBODIMENTS

As illustrated in FIGS. 1–4 and 9, the first embodiment of the ball pressure testing device 20 comprises a housing having two half-shells 2 and 4 which are fitted together so that one half shell moves with respect to the other to increase or decrease pressure on the ball 1 that is being tested. As illustrated, the two half shells 2,4 are cylindrical, with lower half shell 4 having an outer diameter slightly smaller than the inner diameter of the upper half shell 2 so that the two shell moved telescopically along a central axis 5. For a device intended for measuring tennis balls the housing is generally the same size as a tennis ball can. Exemplary dimensions for the device for testing tennis balls are an outer diameter of 76.2 mm (3.0 in.) and an inner diameter of 69.85 mm (2.75 in.) for the upper half shell 2, and 68.6 mm o.d. (2.7 in.) and 62.2 mm i.d. (2.45 in.) for the lower half shell 4, compared with the diameter of a standard tennis ball, which is 63.5–66.7 mm (2.2–2.62 in.). However, the size and shape of the housing can be any shape that will provide means for retaining the ball and allow relative motion between the two half shells so that the ball can be supported and compressed within them, allowing a small amount of extra expansion room in the device's interior to permit deformation of the ball.

The housing may include a removable base 10 disposed at the bottom of lower half shell 4, which can be attached using screws 15 or other appropriate attachments means. Disposed within base 10 are batteries 9 (shown in FIG. 2), which may be AA, AAA or any suitable battery for powering the electrical indicator devices.

The material of which the housing is constructed is preferably clear acrylic, polycarbonate, or similar plastic or polymer, however, colored, translucent or opaque materials, or some combination thereof, may also be used.

Figure 1:
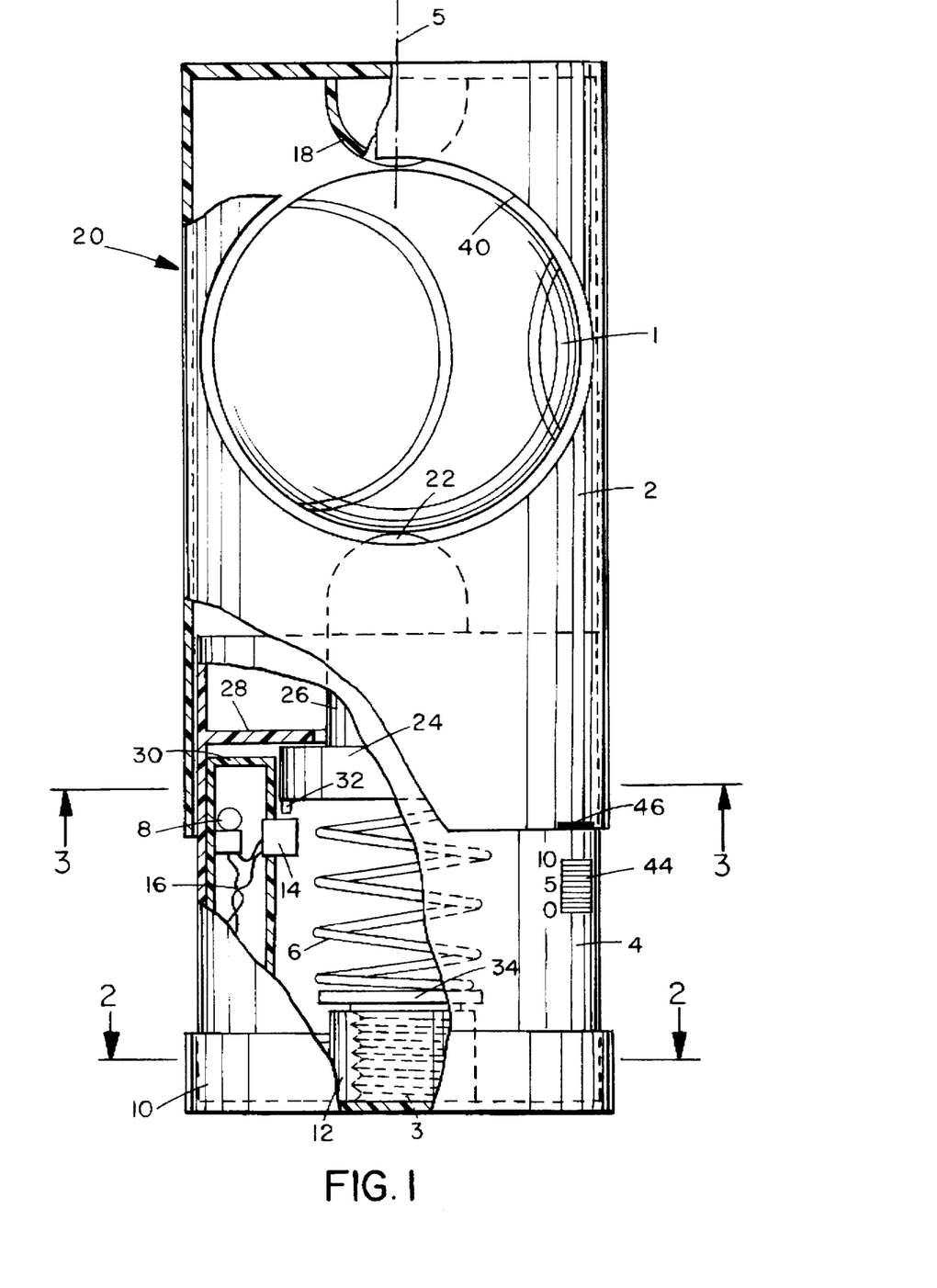
FIG. 1 is a front view, partially cut away, showing a first embodiment of the present invention.

Ball supports 18,22 are disposed within the upper and lower half shells, respectively. An opening in top shell 2 has a diameter that is large enough to insert and remove the ball 1 so that it rests between the ball supports 18,22. Each ball support 18,22 preferably has a focusing surface, i.e., a curvature or point, so that the pressure applied to the ball at the contact points is uniformly focused to a relatively small area, with the focus area coinciding with the central axis 5. This focusing allows a greater ball deformation for a given applied force. As shown, the contact points are semi-spherical at the ends of a cylinder, however, they may be in the shape of a cone, pyramid, frustum, or any shape which provides a focusing of the applied force.

Ball support 18 is fixed within the inner top surface of upper half shell 2 so that it extends downward and does not move relative to the upper half shell 2. Ball support 22 is disposed within lower half shell 4 so that it extends upward, but is movable relative to the lower half shell 4. Ball support 22 is disposed at the upper end of cylinder 26 which is fixedly attached to support base 24. Cylinder 26 has a diameter such that it can move along the central axis 5 within an opening in support base stop 28, which opening has a diameter smaller than that of support base 24 so that support base 24 is prevented from moving upward beyond stop 28. Spring 6 is attached to the bottom of base 24 to bias the ball support 22 upward with a pre-determined reference force $F_R$.

Spring 6 is typically a stainless steel spring pre-compressed to reference force $F_R$ by mounting it on spring base 34 which includes threaded plug 3 that fits within threaded bore 12. In the exemplary embodiment, the spring was a No. C11433 spring from Century Spring Corp. of Los Angeles, Calif. Threaded bore 12 is disposed within the base 10 of lower half shell 4. When threaded plug 3 is rotated so that it moves upward within threaded bore 12, the compression of spring 6 between spring base 34 and support base stop 28 is increased so that greater displacement for a given ball pressure is required to compress spring 6. Similarly, as threaded plug 3 is unscrewed within bore 12, compression decreases, and a lesser displacement is required to compress spring 6.

A displacement scale 44 consisting of a set of reference lines is located on the outside of the lower half shell 4 so that it is axially aligned with a marker 46 on the lower edge of upper half shell 2. The displacement scale 44 may have numbers or other indicators of relative values, e.g., red, yellow, and green for bad, marginal and good, respectively. The lowest point on the scale will correspond to an unacceptably de-pressurized ball, with the divisions between the top and the bottom representing values between the pressure of a new ball and that of an unacceptable ball.

Figure 9:
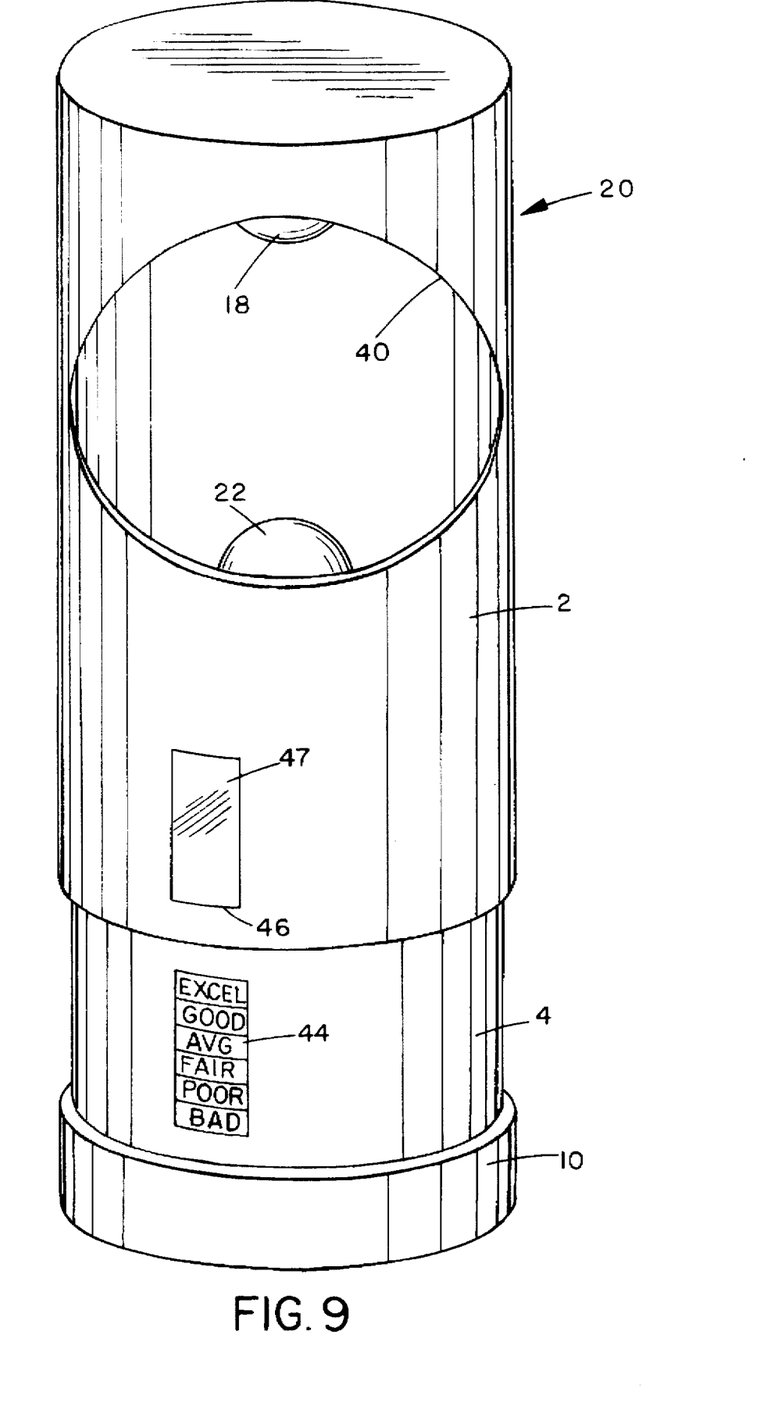
FIG. 9 is a perspective view of an exemplary embodiment of the invention.

As the upper half shell 2 and lower half shell 4 are compressed together, the marker 46 moves along the scale 44, providing a relative indication of the ball pressure. Where the material of which the half shells 2,4 are constructed is transparent plastic, or where a transparent window 47 (shown in FIG. 9) is provided, the displacement scale 44 and marker 46 can be positioned interchangeably, with the only requirement being that the superimposed scale 44 and marker 46 can be viewed to determine relative displacement. In FIG. 9, for example, compression of half shells 2, 4 causes transparent window 47 to overlay scale 44. The alignment of marker 46, formed by the bottom edge of window 47, against scale 44 determines relative displacement and, thus, the ball's condition (i.e., "EXCEL", "GOOD", "AVG", "FAIR", "POOR" or "BAD").

Located within lower half shell 4 is electric switch 14 and indicator lamp 8, which are connected via twisted wire pair 16 to a battery (not shown) which may be disposed within the base 10. Electric switch 14 is a contact switch which is wired to conduct current from the battery to the indicator lamp 8 when contact 32 completes the circuit. Contact 32 is attached to base 24 such that the switch 14 is activated when the spring 6 is compressed sufficiently to make contact between switch 14 and contact 32. The indicator lamp 8 may be any illuminating device, including simple incandescent flashlight-type bulbs and LEDs. When the material of which the half shells 2, 4 are constructed is opaque, a transparent window 50 (shown in FIG. 4) is provided such that light from indicator lamp 8 can be seen by the user. An illuminating indicator may be replaced or augmented by audible indicators.

Reference force $F_R$ is the force required to deform a new or "standard" ball to the point at which switch 14 is activated and indicator lamp 8 is illuminated. The ability to set the reference force $F_R$ allows compensation for differences in ball pressures due to altitude or air temperature, such as exist among the world-wide distribution of tennis courts.

Set-up of the testing device 20 is achieved by inserting the "standard" ball through opening 40 so that it is supported within the interior walls of the upper half shell 2 between ball supports 18,22. The user presses down on the top of upper half shell 2 causing the ball 2 to be compressed and deformed until sufficient applied downward force $F_A$ is applied to slightly exceed the pre-compressed spring reference force $F_R$, and to align marker 46 with the highest level on reference scale 44. (Note that the applied force need not literally be "downward", but merely compressive, such that the testing device 20 will be equally effective if it is held within the user's hands and squeezed together.) At this point, indictor lamp 8 should be illuminated. If not, plug 3 should be adjusted upward until the indictor light 8 can be activated by slightly exceeding the spring reference force and aligning the marker 46 with reference scale 44. If indicator light 8 is turned on before marker 46 and the highest level on displacement scale 44 are aligned, plug 3 should be backed off so that more displacement is required to turn on lamp 8. This "zeroes" or calibrates the device.

Figure 4:
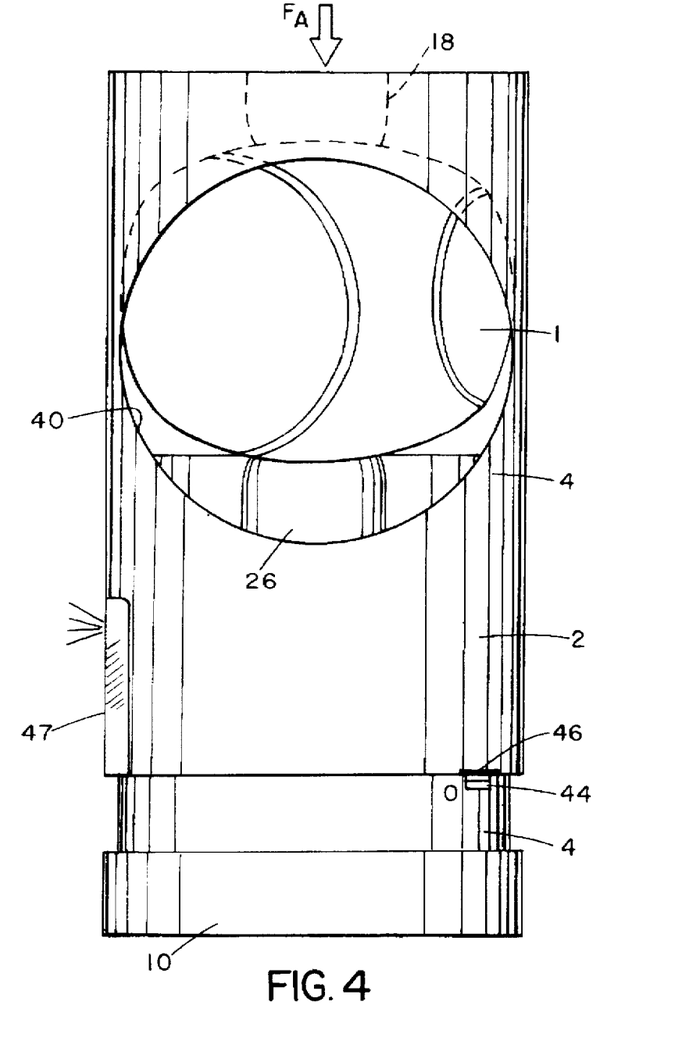
FIG. 4 is a front view of the first embodiment with force applied to compress the pressurized ball being tested.

To measure other balls, the ball to be tested is inserted into the device 20 and the upper and lower half shells 2,4 are pressed together to deform the ball. As soon as the indicator lamp 8 is lit, the user knows that the ball 1 has been deformed to the standard pressure or less. As illustrated in FIG. 4, the numbers (or other values) on the displacement scale 44 will provide a relative value indicating the ball deformation. A greater displacement means that the ball has less internal pressure and is, therefore, less suitable for use.

Figures 2, 3, 5:
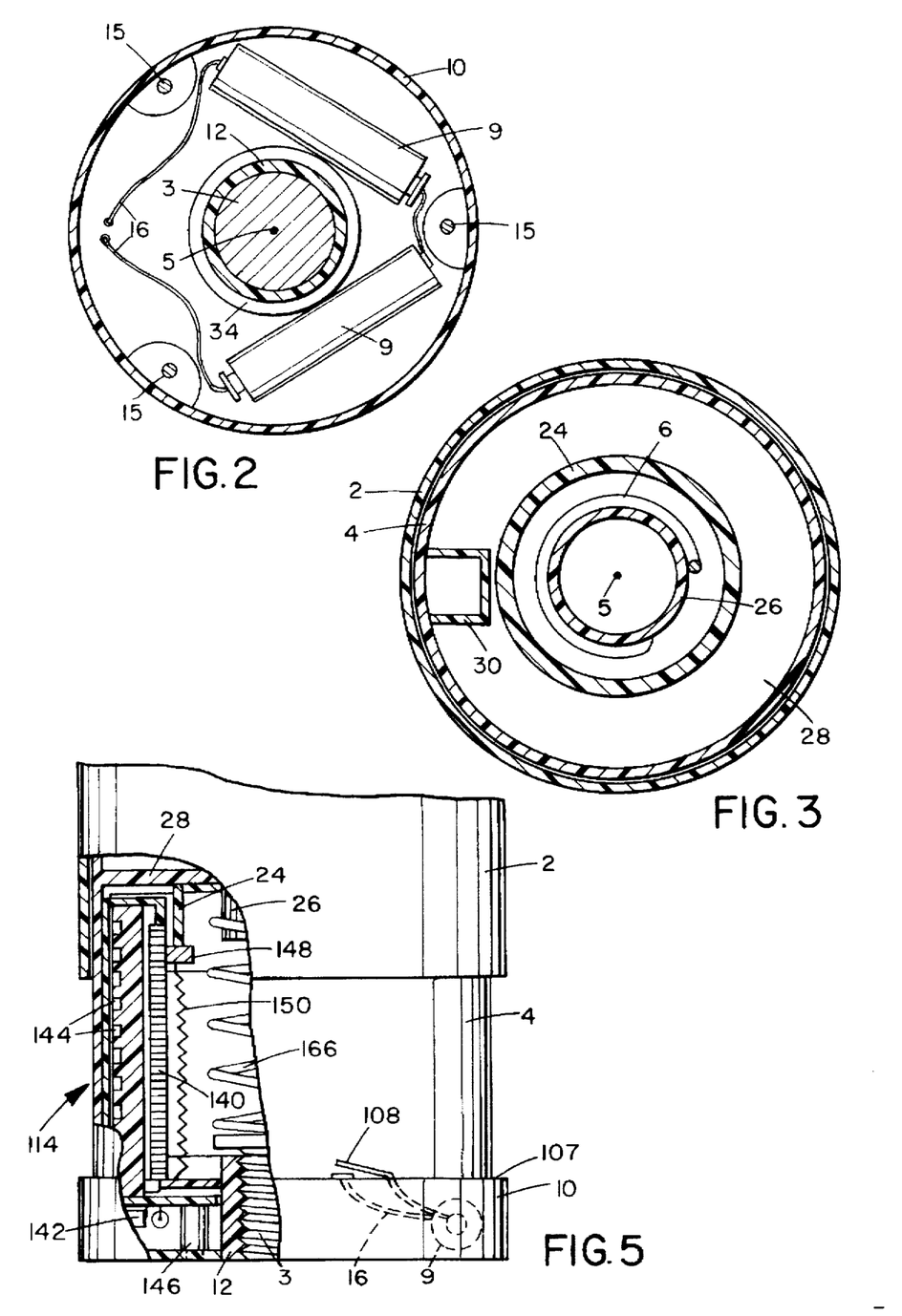
FIG. 2 is a cross-section taken along line 2—2 of FIG. 1.
FIG. 3 is a cross-section taken along line 3—3 of FIG. 1.
FIG. 5 is a partial front view, partially cut away, of a second embodiment of the invention.

Referring next to FIG. 5, the measurement mechanism of a second embodiment of the invention is illustrated, which mechanism is based upon a different principle than the previous embodiment. Whereas the previous embodiment is based on a constant force principle, the second embodiment is based on a constant displacement principle.

As in the first embodiment, the ball pressure testing device 120 of the second embodiment comprises a housing having two half-shells 2 (shown only partially) and 4 which are fitted together so that one half shell moves with respect to the other to increase or decrease pressure on the ball (not shown) that is being tested. The two half shells 2,4 are cylindrical, with lower half shell 4 having an outer diameter slightly smaller than the inner diameter of the upper half shell 2 so that the two shell moved telescopically along a central axis.

The housing may include a removable base 10 disposed at the bottom of lower half shell 4, which can be attached using appropriate attachments means. Disposed within base 10 are batteries (not shown in FIG. 5).

The ball supports and other elements of the device are as described for the first embodiment. As above, spring 166 is typically a stainless steel spring mounted on spring base 34 which includes threaded plug 3 that fits within threaded bore 12. In the exemplary embodiment the selected spring was a No. C830 spring available from Century Spring Corp., Los Angeles, Calif. Threaded bore 12 is disposed within the base 10 of lower half shell 4. When threaded plug 3 is rotated so that it moves upward within threaded bore 12, the compression of spring 166 between spring base 34 and support base stop 28 is increased so that greater displacement is required to compress spring 166. Similarly, as threaded plug is unscrewed within bore 12, compression decreases, and a lesser displacement is required to compress spring 166.

In the second embodiment, the ball pressure measurement device is fully depressed to the set displacement stop 107 by applying the force $F_A$. Full displacement actives switch 108, which is connected to wires 16 and battery 9, to turn the power on. The required force $F_A$ indirectly represents the internal pressure of the ball under the reference displacement. Balls that have less pressure will require a lower force $F_A$ when they are deformed to the reference displacement. The force $F_A$ is measured and displayed on LED bar graph display 114. In the exemplary embodiment, the bar graph display was #276-081 from Radio Shack (Tandy Corporation). The force $F_A$ is measured by compressing spring 166, which compression moves the slide 148 on sliding potentiometer 140. Spring 150 provides a restoring force to potentiometer slide 148 to reduce backlash. In the exemplary embodiment, slide 148 was carbon slide potentiometer Part No. 448XD2103BDN from CTS Corporation. As a result of the compression, sliding potentiometer 140 produces a voltage output proportional to the spring displacement and, therefore, the applied force $F_A$. The voltage level is detected and encoded by bar graph driver electronic apparatus 142 (bar graph display driver #2M3914 from National Semiconductor), wherein the voltage output from potentiometer 140 is converted to a digital code that is subsequently decoded to turn on a specific Light Emitting Diode (LED) 144 within the series of contiguous LEDs of the bar graph display 114. The particular LED 144 activated in the bar graph display 114 represents the relative value of the applied force $F_A$ and, thus, the ball pressure.

The ball pressure measurement device of the second embodiment is calibrated to span the range from a 'new' ball to a 'worst case' used ball at the then existing atmospheric conditions (i.e., altitude (barometric pressure), and temperature). The new ball (a "good standard" ball) and a 'worst case' used ball (a "bad standard" ball) serve as reference balls. First, the used ball is placed in the device and the displacement apparatus is depressed to the full reference displacement, the activation of a lowest bar graph element 144 of the bar graph display 114 is adjusted by turning adjustment screw 3, thereupon, in order that the spring force representing the pressure in the 'used reference' ball can be increased or decreased until the desired lowest bar graph display element 144 is activated. This establishes the lowest ball pressure that will activate a bar graph element. The 'new reference' ball that is typically a new ball with high internal pressure is placed in the device.

When the device is depressed to the full reference displacement, the activation of a specific LED 144 is adjusted by turning adjustment screw 146 so that the voltage representing the reference force can be increased or decreased until the desired top LED 144 is activated. Once adjusted, the reference force value will have been preset to a reference force (pressure) that represents the 'good' ball, which ball will serve as the current 'standard ball' for comparing (match-testing) a set of other balls. The ability to adjust the upper and lower reference forces allows for adjustments to be made to represent the lowest ball pressure of interest allows for adjustments to be made for measuring the range of internal ball pressure changes due both to differences between balls and to differences in the altitudes and temperatures of playing fields, such as tennis courts.

Figure 6:
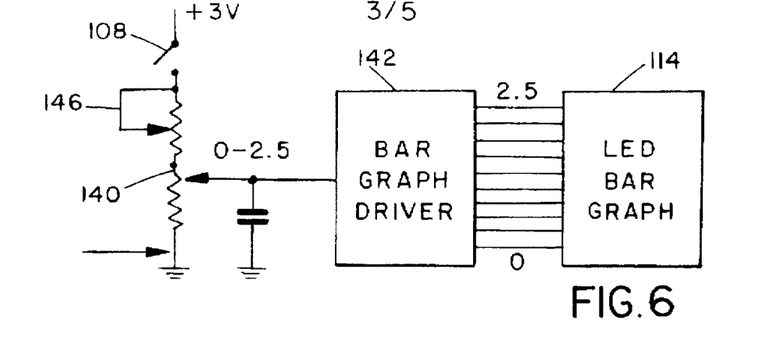
FIG. 6 is a circuit diagram showing the electronic components of the second embodiment.

FIG. 6 provides a block diagram of the circuit for operation of the second embodiment. As illustrated, adjustment screw 146 adjusts the range at the high end so that the top LED 144 can be activated. Potentiometer 140 provides variable voltage based upon the 3V operating voltage supplied by the batteries, with an output range of 0 to 2.5V. The output voltage of the potentiometer 140 is fed to bar graph driver 142, which, in the preferred embodiment, is an LM3914 integrated circuit. Bar graph driver 142 selects the appropriate LED 144 of LED bar graph 114 to activate based upon the received voltage level from potentiometer 140.

Figure 7:
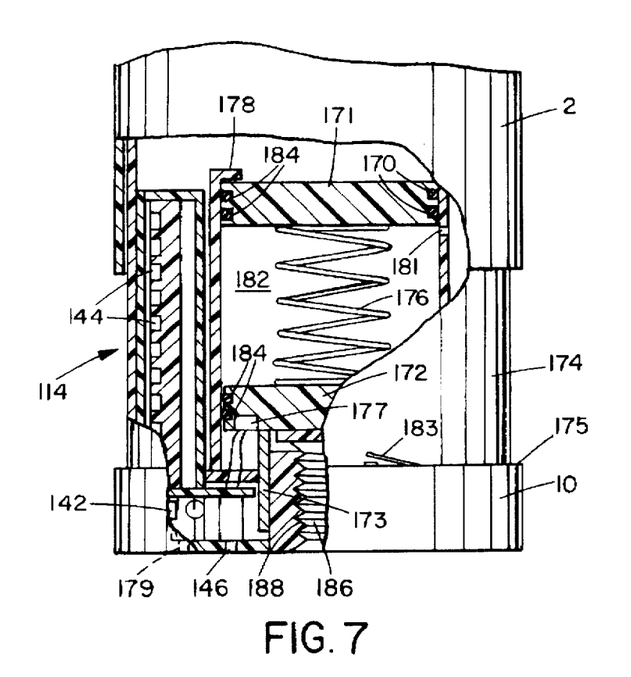
FIG. 7 is a partial front view, partially cut away, of an alternate version of the second embodiment of the invention.

Referring now to FIG. 7, an alternative configuration of the second embodiment is illustrated. In this embodiment, the ball supports and other elements of the device are as described for the first and second embodiments. The difference lies in that spring 166 is replaced with an air spring, and a pressure transducer is provided to detect changes in air pressure, i.e., compression.

Air is compressed within cylindrical compression chamber 182 by moving upper piston 171, which is attached to ball support 22, downward within compression cylinder 178. The volume of compression chamber 182 may be adjusted by turning threaded plug 186 within threaded bore 188 to adjust the device for different local ambient atmospheric pressures such as are encountered at different altitudes. Threaded plug 186 moves lower piston 172 up or down within compression chamber 182, to decrease or increase the trapped air volume, respectively. One or more O-rings 170 (in this case, two are shown at each location) are fitted within corresponding circular grooves 184 in the upper and lower pistons 171 and 172 to provide pressure seals within the compression cylinder 178. Guide 173 is added to piston 172 to prevent it from rotating when threaded plug 186 is turned to adjust the chamber volume. A light spring 176 provides a small restoring force to return piston 171 to the top of compression cylinder 178 when applied force $F_A$ is removed. A bleed hole 181 permits equalization of the pressure in the chamber 182 with ambient pressure when piston 171 is forced upward by spring 176 to the top of compression cylinder 178.

As in the first configuration of the second embodiment, the ball pressure measurement device is fully depressed to the set displacement stop 175 by applying force $F_A$. Full displacement activates microswitch 183 to turn power on. As before, the required force $F_A$ indirectly represents the internal pressure of the ball under the reference displacement. Balls that have less pressure will require a lower force $F_A$ when they are deformed to the reference displacement. The force $F_A$ is measured and displayed on LED bar graph display 114, as above. The pressure in compression chamber 182 is detected by pressure sensor 177, which, in the exemplary embodiment, is surface mount pressure sensor #NPP-301-100A, available from Lucas NovaSensor. As a result of the compression, pressure sensor 177 produces a voltage output proportional to the chamber pressure, and, therefore, the applied force $F_A$. The voltage level is detected and amplified by amplifier 180, whose gain can be adjusted by turning adjustment screw 146. The voltage level from amplifier 180 is detected and encoded by bar graph driver apparatus 142, as described above.

Figure 8:
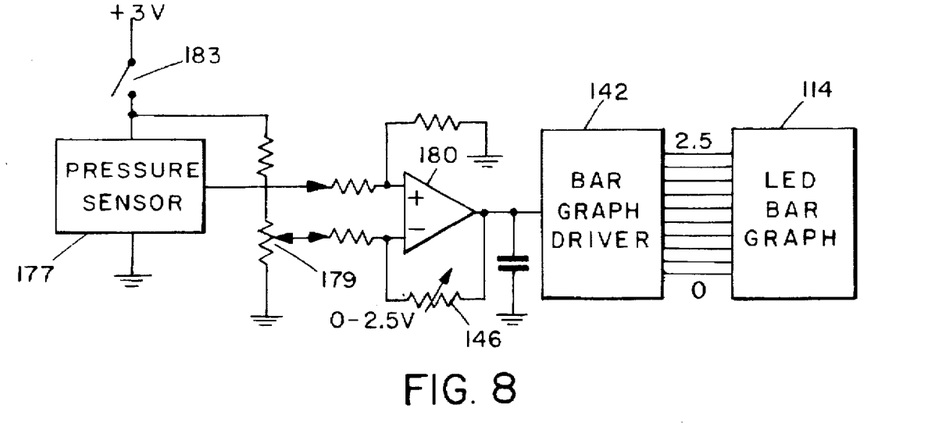
FIG. 8 is a circuit diagram showing the electronic components of the embodiment of FIG. 7.

FIG. 8 provides a block diagram of the circuit for operation of the embodiment of FIG. 7. As illustrated, adjustment screw 146 adjusts the range of the high end so that the top LED 144 can be activated, and adjustment screw 179 adjusts the low voltage limit of the circuit for turning on the lowest pressure LED (indicating a bad ball), which assists in minimizing discharge of the batteries when the device is not in use. Pressure sensor 177 provides variable voltage based upon the 3 V operating voltage supplied by the batteries. Amplifier 180 provides an output range of 0V to 2.5V. Output voltage amplifier 180 is fed to bar graph driver 142. In the embodiment, the LED bar graph and other circuit elements are as described in the first alternative configuration.

In view of the preceding description of exemplary embodiments, it will be appreciated that the invention has achieved an ability to accurately measure the internal pressure of an inflated ball for purposes of separating balls into various pressure groups ranging from 'new' to unplayable. These matched groups can then be used for consistency in competitive match play and training. While the described embodiments are directed toward use with tennis balls, other types of balls may be measured by constructing the described devices with the appropriate dimensions for the selected ball.

Other known devices, including the combination of a spring and linear displacement transducer, or a piezoelectric crystal or a strain gauge load cell, can be used to measure the force on the ball. Using such devices may facilitate the use of other mechanical arrangements, i.e., other than concentric sliding cylinders, that could be used to guide the protrusions together from opposite sides of the ball. Thus, the physical configuration of the housing is not limited to a single cylinder within which the ball may be placed, but may be, for example, a pair of telescoping tubes (of nearly any cross-sectional shape) attached to each of a base and a top, each of which has a ball support located between the pair of tubes, so that the ball is placed between the tubes and the base and top are pressed together.

It will be evident that there are additional embodiments which are not illustrated above but which are clearly within the scope and spirit of the present invention. The above description and drawings are therefore intended to be exemplary only and the scope of the invention is to be limited solely by the appended claims.

We claim:

1. A device for determining relative pressure in a pressurized ball, the ball having a first diameter, the device comprising:

a housing having a first half and a second half, each of said first half and said second half having an inner dimension greater than the first diameter of the ball, and one of said first half and said second half having a first inner dimension greater than an outer diameter of the other half so that at least a portion of each of said first half and said second half interfit telescopically and one of said first half and said second half can be moved along a central axis with respect to the other half;

an opening in said housing for inserting the ball into the housing;

a pair of ball supports centered along the central axis and disposed on diametrically opposite sides of said opening, a first ball support of said pair being attached to said first half and a second ball support being attached to said second half, said first ball support being fixedly attached said first half and said second ball support being slidable within said second half along the central axis;

a spring means disposed within said second half for biasing said second ball support toward said first ball support at a pre-determined spring force;

spring adjustment means for varying the pre-determined spring force;

measurement means for determining a displacement of said second ball support within said second half of said housing when said first half and said second half are compressed together along the central axis;

a visible display means for displaying the displacement measured by said measurement means; and a power supply for providing an operating current;

wherein at least one of said measurement means and said visible display means is electrical.

2. A device as in claim 1 wherein said visible display means includes an electrical indicator and a printed displacement scale and said displacement measurement means includes an electrical switch for connecting said power supply to said electrical indicator and a marker for comparison to said printed displacement scale, wherein said electrical switch conducts operating current to said electrical indicator for a first range of displacement corresponding to a standard ball pressure and said marker is compared against said printed displacement scale for a second range of displacement after the standard ball pressure is indicated.

3. A device as in claim 1 wherein said visible display means is an LED display and said displacement measurement means is a potentiometer and a potentiometer slide, wherein said potentiometer converts said operating current from said power supply into an LED drive voltage having a level representative of the relative displacement of said potentiometer slide along said potentiometer, wherein said LED drive voltage is for activating said LED display.

4. A device as in claim 3 wherein said LED display is a bar graph having a plurality of LEDs.

5. A device as in claim 4 wherein each LED of said plurality of LEDs is activated by a corresponding said LED drive voltage of a plurality of different LED drive voltages.

6. A device as in claim 5 wherein said plurality of different LED drive voltages includes a range of drive voltages, a first end of said range corresponding to a full displacement of said top half of said housing with respect to said bottom half of said housing, said full displacement being determined by measuring a bad standard ball.

7. A device as in claim 6 wherein a second end of said range corresponds to a minimum displacement of said top half of said housing with respect to said bottom half of said housing, said minimum displacement being determined by testing a good standard ball.

8. A device as in claim 3 further comprising a restoring spring attached to said potentiometer slide for providing a restoring force.

9. A device as in claim 1 wherein said second ball support is disposed on top of a piston which is slidably enclosed within a compression chamber, said piston being slidable along the central axis, and said measurement means is a pressure sensor for detecting a compression of air within said compression chamber when said piston is moved along the central axis, wherein said pressure sensor generates a voltage representative of a relative pressure in said compression chamber.

10. A device as in claim 9 wherein said visible display means is an LED display and the voltage representative of relative pressure provides an LED drive voltage for activating said LED display.

11. A device as in claim 10 wherein said LED display is a bar graph having a plurality of LEDs.

12. A device as in claim 1 where each of said top half and said bottom half are generally tube-shaped.

13. A device as in claim 12 wherein each of said top half and said bottom half are cylindrical.

14. A device as in claim 1 wherein the pressurized ball is a tennis ball and said housing has approximate dimensions of a tennis ball can.

15. A device as in claim 1 wherein each of said first ball support and said second ball support has a focusing point at a contact surface with the ball.

16. A device as in claim 15 wherein said focusing point is semispherical.

17. A method for determining an internal pressure within a pressurized ball, the method comprising:

supporting the pressurized ball between a first ball support and a second ball support each disposed within a housing, said second ball support being disposed diametrically opposite said first ball support with respect to the pressurized ball, said second ball support having a bias spring for providing a reference biasing pressure toward said first ball support, said first ball support being fixed with respect to a first half of said housing, said second ball support being movable with respect to a second half of said housing and said first half and said second half being movable with respect to each other;

providing a displacement scale being in a fixed relationship to said second half of said housing for measuring a displacement of said second ball support within said second half of said housing;

applying an initial force to move said first half and said second half of said housing together to compress the pressurized ball between said first ball support and said second ball support so that the reference biasing pressure is just exceeded;

applying an additional force to move said first half and said second half of said housing together to deform the pressurized ball so that said second ball support moves with respect to said second half of said housing; and indicating a displacement of said second ball support within said second half of said housing to provide a measurement of the internal pressure within said pressurized ball.

18. The method of claim 17 wherein the step of indicating a displacement includes electronically displaying a displacement relative to a good standard ball.

19. The method of claim 18 further comprising electronically displaying the displacement relative to a bad standard ball.

20. A method for match-testing a plurality of pressurized balls, each pressurized ball having an internal pressure, the method comprising:

(a) supporting a good standard ball between a first ball support and a second ball support each disposed within a housing, said second ball support being disposed diametrically opposite said first ball support with respect to the pressurized ball, said second ball support having a bias spring for providing a reference biasing pressure toward said first ball support, said first ball support being fixed with respect to a first half of said housing, said second ball support being movable with respect to a second half of said housing and said first half and said second half being movable with respect to each other;

(b) providing a displacement scale being in a fixed relationship to said second half of said housing for measuring a displacement of said second ball support within said second half of said housing;

(c) applying an initial force to move said first half and said second half of said housing together to compress the good standard ball between said first ball support and said second ball support;

(d) adjusting the reference biasing pressure of the bias spring so that the displacement of said second ball support within said second half corresponds to a best point on the displacement scale;

(e) releasing the initial force and removing the good standard ball from between said first and second ball supports;

(f) supporting a first ball of the plurality of pressurized balls between said first and second ball supports;

(g) compressing the first ball between the first and second ball supports by applying the initial force to move said first half and said second half of said housing together so that the reference biasing pressure is just exceeded;

(h) applying an additional force to move said first half and said second half of said housing together to deform the first ball so that said second ball support moves with respect to said second half of said housing;

(i) indicating a displacement of said second ball support with respect to said displacement scale to provide a measurement of the internal pressure within the first ball relative to the good standard ball; and (j) removing the first ball and repeating steps (f) through (j) for each remaining ball of said plurality of pressurized balls until said plurality of pressurized balls has been tested.

* * * * *